US006531616B2

(12) United States Patent
Puts et al.

(10) Patent No.: US 6,531,616 B2
(45) Date of Patent: Mar. 11, 2003

(54) PROCESS FOR THE PREPARATION OF A-METHYLENELACTONES AND A-SUBSTITUTED HYDROCARBYLIDENE LACTONES

(75) Inventors: Rutger D. Puts, Wilmington, DE (US); Charles Brandenburg, Wilmington, DE (US); Kenneth R. Tarburton, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/029,566

(22) Filed: Dec. 21, 2001

(65) Prior Publication Data

US 2002/0143195 A1 Oct. 3, 2002

Related U.S. Application Data

(60) Provisional application No. 60/257,957, filed on Dec. 22, 2000.

(51) Int. Cl.[7] ............... C07D 313/00; C07D 309/00; C07D 307/02

(52) U.S. Cl. .............. 549/266; 549/272; 549/273; 549/295

(58) Field of Search ............. 549/295, 273, 549/272, 266

(56) References Cited

U.S. PATENT DOCUMENTS 5,166,357 A    11/1992  Orlek et al.
6,323,474 B1 *  5/2001  Brandenburg et al. ...... 549/266

\* cited by examiner

*Primary Examiner*—Amelia Owens
(74) *Attorney, Agent, or Firm*—Inna Y. Belopolsky

(57) ABSTRACT

This invention pertains to a process for making α-methylenelactones and α-substitute hydrocarbylidene lactones. More specifically, the present invention obtains high yields of α-methylene-γ-butyrolactone by heating γ-butyrolactone and diethyl oxalate in the presence of a base. The second step comprises treatment of the α-oxalyl enolate salt with formaldehyde to afford the α-methylene-γ-butyrolactone.

44 Claims, No Drawings

PROCESS FOR THE PREPARATION OF A-METHYLENELACTONES AND A-SUBSTITUTED HYDROCARBYLIDENE LACTONES

FIELD OF THE INVENTION

This invention is in the field of synthetic organic chemistry. This invention pertains to a method to produce α-methylenelactones and α-substituted hydrocarbylidene lactones. More specifically, this invention pertains to a simple, efficient and economic method to produce α-methylene-γ-butyrolactone from γ-butyrolactone.

TECHNICAL BACKGROUND OF THE INVENTION

α-Methylenelactones have been the subject of intensive synthetic studies. Specifically, the α-methylene-γ-butyrolactone group is an important structural feature of many sesquiterpenes of biological importance. In addition, α-methylene-γ-butyrolactones are regarded as potential key monomers in both homopolymers and copolymers. One main use for α-methylene-γ-butyrolactone is as an intermediate for the production of 3-methyltetrahydrofuran. Currently the cost of α-methylene-γ-butyrolactone is too high to warrant commercial production of the resulting polymers. Some of the current synthetic routes suffer from low yields, byproduct formation and expensive starting materials.

An early synthesis of α-methylene-γ-butyrolactone involves two steps (Martin et al., *J. Chem. Soc.* D 1:27 (1970)). The first is carboxylation of γ-butyrolactone with methyl methoxymagnesium carbonate (Stiles' reagent) to produce the acid. Next, the acid is briefly treated with a mixture of aqueous formaldehyde and diethylamine, followed by a separate treatment of the crude product with sodium acetate in acetic acid. The first step requires 6–7 hours and affords almost quantitative yields, whereas the second step can be accomplished in less than 30 minutes but with yields of only 50%.

Murray et al. (*Synthesis* 1:35–38 (1985); see also U.S. Pat. No. 5,166,357) disclose a route to α-methylene-γ-butyrolactone that also involves a two-step sequence consisting of the reaction of γ-butyrolactone with ethyl formate in the presence of base, followed by refluxing the resulting α-formyl-γ-butyrolactone sodium salt under nitrogen with paraformaldehyde in tetrahydrofuran. Distillation affords the desired α-methylene-γ-butyrolactone as a colorless oil. This reaction sequence can best be explained by formyl transfer from carbon to oxygen followed by elimination of carboxylate anion.

Essentially all approaches to α-methylene-γ-butyrolactone are liquid-phase processes. One exception is the vapor-phase process described in JP 10120672, which involves subjecting γ-butyrolactone or an alkyl-substituted γ-butyrolactone, in which one or more hydrogen atoms at the β- or γ-position of the γ-butyrolactone are substituted with $C_1$–$C_{18}$ alkyl groups, to a gaseous phase catalytic reaction using a raw material gas containing formaldehyde or its derivative in the presence of a catalyst. Molecular oxygen is preferably added to the raw material gas and the catalyst is preferably silica alumina catalyst. Specifically, a gaseous mixture of γ-butyrolactone, formaldehyde, water, nitrogen and oxygen are passed through a reactor packed with Wakogel C-200, pretreated with an aqueous potassium hydroxide solution and heated at 330° C., to afford α-methylene-γ-butyrolactone at a conversion of 35.5% and a selectivity of 46.9%.

The synthetic approaches to date typically involve two-step processes that use highly flammable solvents such as tetrahydrofuran (THF) or diethyl ether. Impurities are often present at high concentrations and the final distillation leaves significant amounts of residual polymer. In McMurry's synthesis of α-methylene-γ-butyrolactone (*J. Org. Chem.* 42:1180–5 (1977)), a solution of γ-butyrolactone and diethyl oxalate is added to a cooled solution of sodium ethoxide in ethanol. The α-oxalyl sodium salt is formed in solution. The solvent is removed in vacuo and the residual pasty material is taken up in water and diethyl ether and then acidified to give the α-ethyl oxalyl γ-butyrolactone (vide infra). This compound is then dissolved in THF and added to a cooled suspension of lithium hydride in THF. Formaldehyde gas is bubbled in to produce α-methylene-γ-butyrolactone. The final overall yield is reported to be 83%. While this process affords α-methylene-γ-butyrolactone in fairly high yield and purity, it is not readily adapted to large scale reactions required for polymer production.

Although the above methods for the production of α-methylene-γ-butyrolactone and α-substituted hydrocarbylidene lactones are useful, they are time consuming and do not obtain high product purity. In addition, the known methods are not readily adaptable to large scale reactions. Another problem is to find a more effective and economical method of production than are currently available. The present method offers a user-friendly process resulting in high yields and good selectivity. Furthermore, the process eliminates high levels of the residual γ-butyrolactone starting material which has been shown to limit the scope of polymerization methods used in the production of α-methylene-γ-butyrolactone. The critical advance is the isolation of the intermediate compound which is crucial in obtaining high purity of the α-methylene-γ-butyrolactone and α-substituted hydrocarbylidene lactone product as a result of the method presented herein.

SUMMARY OF THE INVENTION

The instant invention relates to a process for preparing α-methylenelactones of Formula III comprising the steps:

(a) contacting lactones of Formula I with an oxalate in the presence of a base and a solvent to form an intermediate mixture comprising the compound of Formula II and isolating the compound of Formula II from the intermediate mixture (b) treating the isolated compound of Formula II with formaldehyde to form a product mixture; and (c) optionally isolating the α-methylenelactones of Formula III from the product mixture.

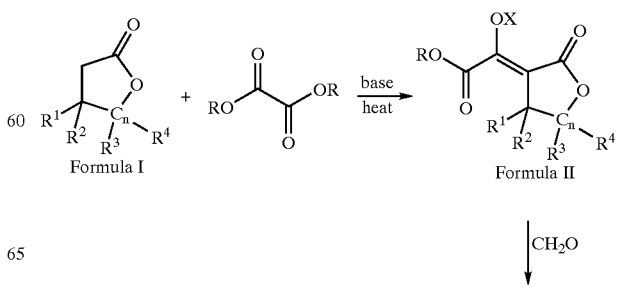

-continued

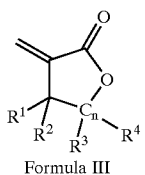

Formula III wherein,
n=1–11;
R is hydrocarbyl or substituted hydrocarbyl;
X is a cation; and
$R^1$, $R^2$, $R^3$ and $R^4$, taken independently are hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aromatic ring, and unsubstituted or substituted aromatic ring containing at least one heteroatom.

The invention further provides a process for the preparation of compounds of Formula III wherein any two of $R^1$, $R^2$, $R^3$ and $R^4$ are members of a ring structure selected from the group consisting of, unsubstituted or substituted cycloalkyl, unsubstituted or substituted cycloalkyl containing at least one heteroatom in the ring, unsubstituted or substituted aromatic ring, and unsubstituted or substituted aromatic ring containing at least one heteroatom in the ring.

Another embodiment of the invention is a process for preparing α-substituted hydrocarbylidene lactones of Formula IV comprising the steps:

(a) contacting lactones of Formula I with an oxalate in the presence of a base and a solvent to form an intermediate mixture comprising the compound of Formula II and isolating the compound of Formula II from the intermediate mixture;

(b) treating the isolated compound of Formula II with a formaldehyde derivative to form a product mixture; and (c) optionally isolating the α-substituted hydrocarbylidene lactones of Formula IV from the product mixture.

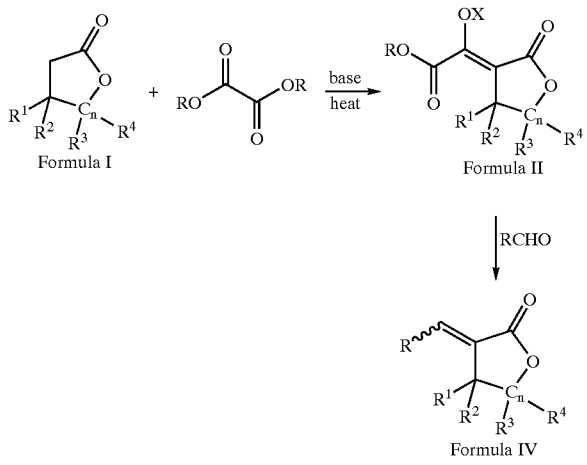

wherein,
n=1–11;
R is hydrocarbyl or substituted hydrocarbyl;
X is a cation; and
R is hydrocarbyl or substituted hydrocarbyl; and
$R^1$, $R^2$, $R^3$ and $R^4$ taken independently are hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aromatic ring, and unsubstituted or substituted aromatic ring containing at least one heteroatom.

The invention further provides a process for the preparation of compounds of Formula IV wherein any two of $R^1$, $R^2$, $R^3$ and $R^4$ are members of a ring structure selected from the group consisting of, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom in the ring, unsubstituted or substituted aromatic ring, and unsubstituted or substituted aromatic ring containing at least one heteroatom in the ring.

In the first step of the processes the base is metal alkoxide, metal carbonate, oxide, hydroxide or phosphate or mixtures thereof and may be supplied in homogeneous or heterogeneous form. The first step of the process is conducted at a temperature range of at least about 25° C. and a pressure less than or equal to 2000 psi, preferable about 75° C. and atmospheric pressure. The reaction may optionally run at higher temperatures, at about 100° C. to about 120° C. under higher pressures of about 700 psi. The reaction may optionally employ an organic solvent and use a phase transfer catalyst. The second step of the process is conducted at a temperature range of at least about 0° C. and a pressure less than or equal to 2000 psi, preferably 10° C. and atmospheric pressure. The first step of the process can employ any number of solvents or combinations thereof, these include but are not limited to methanol, ethanol and isopropanol. The second step of the process can employ any number of solvents or combinations thereof, these include but are not limited to water, toluene, xylenes, hexanes, ethyl acetate, chlorobenzene, 1,2-dichlorobenzene, acetonitrile, methylene chloride, acetone, methyl ethyl ketone, dimethylacetamide, chloroform, chlorobutane, benzene and 1-chlorobutane.

DETAILED DESCRIPTION OF THE INVENTION

The instant invention relates to a process for preparing α-methylenelactones of Formula III comprising heating lactones of Formula I with an oxalate in the presence of a base and solvent, such as sodium methoxide in methanol, to form the α-oxalyl enolate salt of Formula II (Scheme I). If the R group of the base and the R group of the oxalate are different, a mixture of ester R groups in Formula II is obtained. It is recognized that the Formula II may exist as a mixture of E and Z isomers (vide infra) as described in "Formation of Enolates", Comprehensive Organic Synthesis, 1991, Volume 2, p. 99. The Z enolate (as drawn) is the preferred isomer. This salt is easily prepared on 150 gallon scale and is stable for several months at room temperature. The reaction will work in the absence of a solvent, however the workup would no longer facilitate high space-time yields nor be adaptable to a larger scale process, and would require trituration of the solid reaction mass with a solvent such as petroleum ether. The second step comprises treating the α-oxalyl enolate salt with a formaldehyde source, most preferably aqueous 37% formaldehyde, to give the corresponding α-methylenelactone of Formula II. The "crude" product is greater than 95% pure by gas chromatography (GC) and the final product can be obtained in up to 99.8% purity by GC. The final distillation leaves less than 10% polymer residue in the distillation pot. Compared to previous methods, this process produces α-methylene-γ-butyrolactone and its derivatives of Formula III in higher yield and higher purity from ingredients that are readily available in bulk quantities (γ-butyrolactone, sodium methoxide, methanol, ethanol, methylene chloride, aqueous formaldehyde and potassium carbonate).

Scheme I

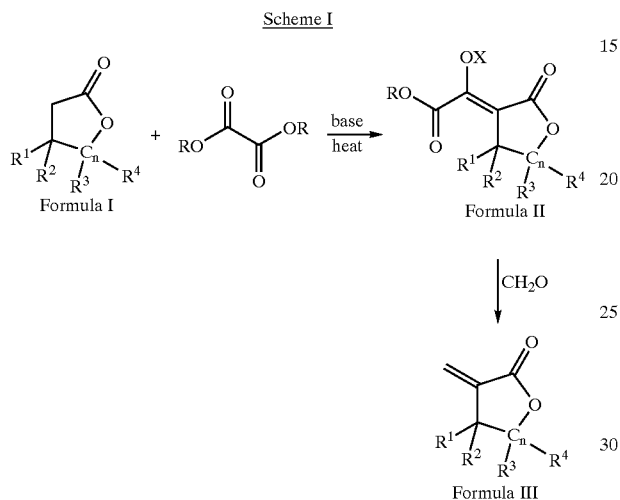

Wherein, n=1–11;

R is hydrocarbyl or substituted hydrocarbyl;

X is a cation; and $R^1$, $R^2$, $R^3$ and $R^4$, taken independently are hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aromatic ring, and unsubstituted or substituted aromatic ring containing at least one heteroatom.

The invention further provides a process for the preparation of compounds of Formula III wherein any two of $R^1$, $R^2$, $R^3$ and $R^4$ are members of a ring structure selected from the group consisting of, unsubstituted or substituted cycloalkyl, unsubstituted or substituted cycloalkyl containing at least one heteroatom in the ring, unsubstituted or substituted aromatic ring, and unsubstituted or substituted aromatic ring containing at least one heteroatom in the ring.

In another embodiment of the invention, the invention provides a process for preparing α-substituted hydrocarbylidene lactones of Formula IV comprising heating lactones of Formula I with an oxalate in the presence of a base and solvent, such as sodium methoxide in methanol, to form the α-oxalyl enolate salt of Formula II (Scheme 2). The second step comprises treating the α-oxalyl enolate salt with a formaldehyde derivative to give the corresponding α-substituted hydrocarbylidene lactone of Formula IV, Scheme 2

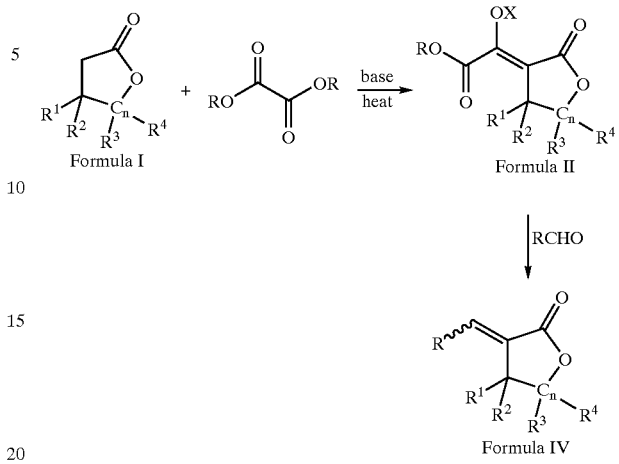

wherein, n=1–11;

R is hydrocarbyl or substituted hydrocarbyl;

X is a cation; and

R is hydrocarbyl or substituted hydrocarbyl; and $R^1$, $R^2$, $R^3$ and $R^4$ taken independently are hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aromatic ring, and unsubstituted or substituted aromatic ring containing at least one heteroatom.

The invention further provides a process for the preparation of compounds of Formula IV wherein any two of $R^1$, $R^2$, $R^3$ and $R^4$ are members of a ring structure selected from the group consisting of, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom in the ring, unsubstituted or substituted aromatic ring, and unsubstituted or substituted aromatic ring containing at least one heteroatom in the ring.

When a group contains a substituent which can be hydrogen, for example $R^1$, $R^2$, $R^3$ and $R^4$, then, when this substituent is taken as hydrogen, it is recognized that this is equivalent to said group being unsubstituted.

In the first step of the processes the base is metal alkoxide, metal carbonate, oxide, hydroxide or phosphate or mixtures thereof and may be supplied in a homogeneous or heterogeneous form. The first step of the process is conducted at a temperature range of at least about 25° C. and a pressure less than or equal to 2000 psi, preferable about 75° C. and atmospheric pressure. The reaction may optionally run at higher temperatures, at about 100° C. to about 120° C. under higher pressures of about 700 psi. The reaction may optionally employ an organic solvent and use a phase transfer catalyst. The second step of the process is conducted at a temperature range of at least about 0° C. and a pressure less than or equal to 2000 psi, preferably 10° C. and atmospheric pressure. The first step of the process can employ any number of solvents or combinations thereof, these include but are not limited to methanol, ethanol and isopropanol. The second step of the process can employ any number of solvents or combinations thereof, these include but are not limited to water, toluene, xylenes, hexanes, acetonitrile, methylene chloride, acetone, methyl ethyl ketone, dimethylacetamide, chloroform, chlorobutane, benzene and 1-chlorobutane. The instant invention may optionally use phase transfer catalysts.

In the context of this disclosure, a number of terms and abbreviations shall be utilized. The following definitions are provided.

An "alkyl" is a straight-chain or branched alkyl, such as, methyl, ethyl, n-propyl, i-propyl, or the different butyl, pentyl and hexyl isomers. Also included are all isomers up to and including octadecyl.

"α-Methylene-γ-butyrolactone" is abbreviated MBL.

"γ-Butyrolactone" is abbreviated GBL.

"Tetrahydrofuran" is abbreviated THF.

"Gas chromatography" is abbreviated GC.

"Nuclear magnetic resonance" is abbreviated NMR.

"Molecular weight" is abbreviated MW.

"Sodium; ethoxycarbonyl-(2-oxo-dihydro-furan-3-ylidene)-methanolate" is also known as ethyl oxalyl γ-butyrolactone sodium salt.

"Sodium; ethoxycarbonyl-(5-methyl-2-oxo-dihydro-furan-3-ylidene)-methanolate" is also known as ethyl oxalyl γ-methyl-γ-butyrolactone sodium salt.

"Sodium; ethoxycarbonyl-(5-penthyl-2-oxo-dihydro-furan-3-ylidene)-methanolate" is also known as ethyl oxalyl γ-pentyl-γ-butyrolactone sodium salt.

A "formaldehyde derivative" is a compound having the general formula RCHO.

An "oxalate" is a compound having the general formula ROC(=O)C(=O)OR, wherein R is hydrogen, hydrocarbyl or substituted hydrocarbyl.

A "cation" is a molecular entity carrying at least one unit of positive charge formally derived from a parent hydride, a parent compound, or a hydro derivative of either, by the gain of one or more hydrons, by the loss of one or more hydride ions, or a combination of these operations.

A "hydrocarbyl group" is a univalent group containing only carbon and hydrogen. If not otherwise stated, it is preferred that hydrocarbyl groups herein contain 1 to about 30 carbon atoms.

A "substituted hydrocarbyl" is a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain from 1 to about 30 carbon atoms. Included in the meaning of "substituted" are heteroaromatic rings.

A "homogeneous base" is a base which is in soluble form and exists in the same phase (solid, liquid or gas) as the reactants.

A "heterogeneous base" is a base which operates on reactions taking place on surfaces where the reacting species are held on the surface of the base by adsorption. Typically heterogeneous bases are not in solution and do not exist in the same phase (solid, liquid or gas) as the reactants.

The terms "E and Z" are generally accepted stereodescriptors of stereoisomeric alkenes $R_1R_2C=CR_3R_4$ ($R_1$ is not equal to $R_2$, $R_3$ is not equal to $R_4$; neither $R_1$ nor $R_2$ need be different from $R_3$ or $R_4$). The group of highest CIP (Cahn-Ingold-Prelog) priority attached to one of the terminal doubly bonded atoms of the alkene (i.e. $R_1$ or $R_2$) is compared with the group of highest precedence attached to the other (i.e. $R_3$ or $R_4$). The stereoisomer is designated as Z (zusammen=together) if the groups lie on the same side of a reference plane passing through the double bond and perpendicular to the plane containing the bonds linking the groups to the double-bonded atoms; the other stereoisomer is designated as E (entgegen=opposite). For the purposes of the instant invention, Formula II can be either the E or Z isomer.

Formaldehyde and Formaldehyde Derivatives

One step of the method is the addition of formaldehyde. Formaldehyde may be supplied in a variety of forms including as a solution (in water, methanol or ethanol) or in the form of a formaldehyde polymer. Polymers of formaldehyde are more generally denominated polyacetals and include or are characterized by a linear polymer chain containing recurring —(CH$_2$O)— units or groups. The preferred polymer of formaldehyde in the composition of the invention is polyoxymethylene which has not been stabilized against thermal degradation as, for example, by end-capping the ends of the linear polymer chain with stabilizing end-groups. Thus, a preferred polymer of formaldehyde is paraformaldehyde, which is a lower molecular weight linear polymer available commercially as a fine powder. Another suitable polymer of formaldehyde is, for example, trioxane. Other polymers of formaldehyde which can be utilized herein are described generally in U.S. Pat. No. 2,768,994, hereby incorporated by reference. Another variety of polymers are sold under the registered trademark Delrin® acetal resins by E. I. du Pont de Nemours and Company, Inc. Delrin® acetal resin polymers are usually stabilized against thermal degradation but may still be utilized in the instant invention.

The method is also successful where a formaldehyde derivative is used in place formaldehyde. One group of suitable formaldehyde derivatives are the substituted aldehydes. When formaldehyde is employed in the reaction the group added to the compound of Formula II, (Scheme 1) will be a methylene group. However, if an alkyl-substituted aldehyde is used, e.g., RCHO (Scheme 2), the new group will be an alkyl-substituted hydrocarbylidene group, that is, RCH=. Examples of suitable substituted aldehydes are acetaldehyde, propionaldehyde, butyraldehyde, isobutyraldehyde, n-pentanal, 2-methylbutanal, 3-methylbutanal, n-hexanal, 2-methylpentanal, 3,3-dimethylbutanal, 2-ethylhexanal, 2-methyidecanal, and also dialdehydes such as glyoxal, methylglyoxal, malonic dialdehyde, succinic dialdehyde and glutaric dialdehyde, and other aldehydes such as 3-hydroxy-2,2-dimethylpropanol (hydro pivalaidehyde), methoxypivalaldehyde, butoxypivalaldehyde, 4-acetoxybutyaldehyde and 5-formylvaleraldehyde.

Bases

The bases of the invention are selected from the metal alkoxides, metal oxides, hydroxides, carbonates and phosphates. The metal alkoxides, oxides, hydroxides, carbonates and phosphates employed herein may be supplied as solutions, powders, granules, or other particulate forms, or may be supported on an essentially inert support as is common in the art of catalysis. Representative bases include, but are not limited to, sodium methoxide, sodium ethoxide, sodium isopropoxide, sodium n-butoxide, potassium carbonate, cesium carbonate, sodium carbonate, barium carbonate, sodium hydrogen carbonate, magnesium oxide, barium oxide, barium hydroxide, lanthanum oxide, potassium hydroxide, cadmium oxide, rubidium oxide, lithium hydroxide, strontium hydroxide, sodium hydroxide, calcium hydroxide, potassium hydroxide, potassium phosphate and mixtures thereof.

The preferred base in the first step is sodium methoxide (Formula I to Formula II). This ingredient is most often supplied as a 25 wt % solution in methanol. Alternatively, sodium ethoxide, sodium isopropoxide, or sodium hydroxide may be used. At atmospheric pressures the temperature of the reaction can range from about 25° C. to about 160° C., with a preferred range of about 70° C. to about 80° C. The process of the present invention may be run at higher temperatures by applying pressures greater than atmospheric.

The bases of the invention may be supported or unsupported. Where a support is desired suitable supports include, but are not limited to, silica, titania, zirconia, alumina, carbon, various zeolites and mixtures thereof.

A base may optionally be used in the second step (Formula II to Formula III and Formula II to Formula IV). The base in the second step is used to neutralize the excess formaldehyde or formaldehyde derivative. This neutralization has been shown to limit byproduct formation (i.e., α-ethyl oxalyl-γ-butyrolactone (Formula V), the spiro compound (Formula VI) and polymerization products—see Example 20). Examples of bases for the second step are ammonia, triethylamine, pyridine, piperidine, pyrrolidinine, pyrrole, dimethylaniline, dimethylaminopyridine, 1,4-diaza[2,2,2]bicycloctane (Dabco), potassium carbonate potassium bicarbonate, sodium carbonate, sodium bicarbonate, calcium carbonate, potassium phosphate, sodium phosphate, sodium acetate, potassium acetate, sodium hydroxide, potassium hydroxide, sodium borate and potassium borate. The preferred base in the second step is potassium carbonate.

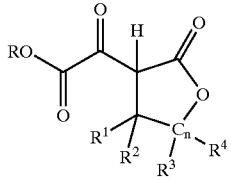

Formula V

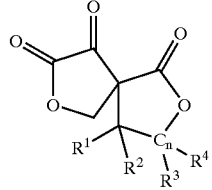

Formula VI

Phase Transfer Catalyst and Solvent Systems

The present method may optionally employ an organic solvent in the first or second step. Suitable organic solvents include but are not limited to toluene, methylene chloride, acetone, acetonitrile, ethyl acetate, ethanol, isopropanol, methanol, 2,2-diethoxypropane, n-butanol and polyethylene glycols. The preferred solvent for use in the first step is ethanol (Formula I to Formula II). The preferred solvent for use in the second step is methylene chloride (Formula II to Formula III).

Where a solvent is employed the instant invention may optionally also use a phase transfer catalyst. Although a wide variety of phase transfer catalysts are known and used in the chemical industry, certain phase transfer catalysts work more effectively than others for a particular chemical reaction and for individual reactants. An example is tetrabutylammonium bromide. Other phase transfer catalysts useful herein include, but are not limited to, quaternary ammonium salts, quaternary phosphonium salts, crown ethers, and polyethers. For polyethers, the phase transfer catalyst is a member selected from the group consisting of polyethylene glycols (PEG's) of various molecular weights (MW). PEG's with an average molecular weight from 200 to >20,000 are available commercially. The number of repeat units, n, in the PEG is an important factor in its effectiveness as a phase transfer catalyst. Values of n greater than or equal to 8 are generally preferred as phase transfer catalysts. The phase transfer catalyst is used in an amount of 0 to 0.25 parts, preferably 0.05 to 0.10 parts, per part by weight of the reactive substrate. Phase transfer catalysts are common and well known in the art, see for example, Cook et al., *Chim. Oggi* 16(1/2):44–48 (1998); "Phase Transfer Catalysis: Fundamentals, Applications, and Industrial Perspectives" by C. M. Starks, C. L. Liotta, and M. Halpern., Chapman & Hall, Inc., 1994.

Isolation Methods

The desired products, including α-methylene-γ-butyrolactone, are isolated using techniques common to the art. For example, when allowed to cool the α-methylene-γ-butyrolactone reaction mixture forms a pale yellow slurry. This slurry is filtered to remove oxalyl by-products. One can optimize the precipitation of the oxalyl by-products with the solvent composition. In ethyl acetate/toluene (1/0 to 1/1 v/v), acetonitrile/toluene (1/1 v/v), acetone/toluene (1/1 v/v), THF/toluene (1/1 v/v), they precipitate from the reaction to make α-methylene-γ-butyrolactone filterable, in toluene or dimethylacetamide it is not. The solvent is then removed in vacuo to give α-methylene-γ-butyrolactone that is greater than 95% pure by GC. The (α-methylene-γ-butyrolactone may be taken to a higher purity by distillation. This distillation can be done in a batch or a continuous mode to give the final product in up to 99.8% purity as a colorless liquid. Vacuum distillation is the preferred method of distillation, since it decreases the amount of polymerization byproducts.

Alternatively α-methylene-γ-butyrolactone can be isolated by steam distillation. Typically, steam is allowed to flow through a distillation apparatus containing α-methylene-γ-butyrolactone. The water distillate (containing α-methylene-γ-butyrolactone) is then extracted with an organic solvent such as ethyl acetate. The solvent is then removed in vacuo to recover α-methylene-γ-butyrolactone.

In another isolation method, α-methylene-γ-butyrolactone can also be purified by melt crystallization. In this process, α-methylene-γ-butyrolactone is cooled below its melting point (below about −35° C.) to form a solid. Liquid impurities are allowed to flow away from the pure, solid α-methylene-γ-butyrolactone. The temperature is then raised to melt the α-methylene-γ-butyrolactone and recover it in a more pure form. The melt crystallization process can be repeated to obtain high purity α-methylene-γ-butyrolactone.

A third isolation method uses a polymerization-depolymerization protocol. A free radical initiator can be added, such an azobisisobutyronitrile or benzoyl peroxide, to the mixture from the second step followed by applying sufficient heat to start a polymerization. A solvent can optionally be added to carry out solution polymerization or use other well known polymerization methods such as bulk and emulsion polymerization. The methylene lactone polymer can then be separated from the by products of this step by well known methods such as precipitation, devolatilization, coagulation or filtration. Once the polymer is obtained in pure form, one can heat it to at least 200° C. to start a depolymerization in which the methylene lactone polymer unzips to form methylene lactone which can be isolated by condensation and possibly further purified by any of the mentioned methods in this patent.

Polymerization Inhibitors (Process Stabilizers)

The instant invention may optionally employ polymerization inhibitors. Examples include phenolic compounds such as monomethylether hydroquinone, hydroquinone, t-butyl catechol (TBC), 2,4-dimethyl-6-tert-butylphenol (Topanol A), 2,6-di-tert-butyl-4-hydroxytoluene (BHT), pentaerythritol, tetrakis(3,5-di-tert-butyl-4-hydroxyhydrocinnamate). Additionally, nitroxides such as 4-hydrox-tetramethylpiperidinoxyl (4-hydroxy-TEMPO), bis(1-oxyl-2,2,6,6-tetramethylpiperidine-4-yl)sebacate can be used. Substituted p-phenylenediamines such as phenothiazine, N,N'-bis(1,4-dimethylpentyl)-p-phenylenediamine, N-(1,4-dimethylpentyl)-N'-phenyl-p-phenylenediamine (Naugard® I-3 (from Uniroyl Co., Middlebury, Conn.)), N-phenyl-N'-isopropyl-p-phenylenediamine, 2-sec-butyl-4,6-dinitrophenol (DNBP), N-phenyl-N'-(1,3-dimethylbutyl)-p-phenylenediamine can also be readily used. Metal complexes such as $CuCl_2$ and $FeCl_3$ can be used too. Furthermore, any mixtures of the above would work in the instant invention. See also Odian, G., In *Principles of Polymerization*, $2^{nd}$ Ed; Wiley Interscience, New York, 1981, p 242 and compounds listed therein.

Preferred inhibitors are compounds with a boiling point 40° C. higher than that of (α-methylenelactone compounds and which do not form an azeotrope with the α-methylenelactone compounds. Specially preferred are N-(1,4-dimethylpentyl)-N'-phenyl-p-phenylenediamine (Naugard® I-3 (from Uniroyal Co., Middlebury, Conn.)), 4-hydroxy-tetramethylpiperidinoxyl (4-hydroxy-TEMPO) and bis(1-oxyl-2,2,6,6-tetramethylpiperidine-4-yl)sebacate in a concentration range of 10 ppm–5 wt %. The preferred concentration is between 0.5–1 wt %.

Reaction Conditions and Processes

The present method lends itself to either batch or continuous processes. In the case of (α-methylene-γ-butyrolactone preparation, a continuous process employs a pipeline reactor for the γ-butyrolactone to α-methylene-γ-butyrolactone conversion. Liquid γ-butyrolactone is fed into a pipe and mixed with diethyl oxalate in the presence of a base. γ-Butyrolactone and diethyl oxalate react to give Formula II as a slurry. This slurry is pumped in to another pipe where formaldehyde is added in a continuous stream. By product solids are filtered and solvent removed to give α-methylene-γ-butyrolactone as a pale yellow liquid. A continuous distillation is then performed to obtain purified α-methylene-γ-butyrolactone.

It is recognized that some reagents and reaction conditions described for preparing compounds of Formula III and Formula IV may not be compatible with certain functionalities present in the lactone starting material (Formula I). In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, $2^{nd}$ ed.; Wiley: New York, 1991). One skilled in the art will recognize that, in some cases, after the introduction of a given reagent as it is depicted in any individual scheme, it may be necessary to perform additional routine synthetic steps to complete the synthesis of compounds of Formula III and Formula IV. One skilled in the art will also recognize that it may be necessary to perform a combination of the steps illustrated in the above schemes in an order other than that implied by the particular sequence presented to prepare the compounds of Formula III and Formula IV.

Preparation of 3-Methyltetrahydrofuran

Where it is desired to reduce α-methylene-γ-butyrolactone to 3-methyltetrahydrofuran, a variety of hydrogenation processes may be coupled with the α-methylene-γ-butyrolactone preparative process, with or without isolation of the intermediate α-methylene-γ-butyrolactone. Typical hydrogenation would involve the reduction of α-methylene-γ-butyrolactone over a hydrogenation catalyst at elevated temperature. Hydrogenation catalysts are common and well known in the art. Those suitable for the present conversion include, but are not limited to, metals such as cobalt, nickel, molybdenum, chromium and palladium.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

Common reagents were purchased from Sigma-Aldrich and solvents from VWR Scientific. NMR spectra were recorded on a Varian VXR-500 spectrometer. Gas chromatography (GC) was performed on a Hewlett-Packard 6890 series instrument running HP Chemstation® software and equipped with an HP-5 (5% Phenyl Methyl Siloxane) column. Pure α-methylene-γ-butyrolactone was synthesized using the method reported by Murray (*Synthesis* 1:35–38 (1985)) for use in GC methods. α-Methylene-γ-butyrolactone was purified by distillation at 0.5 torr/65° C. to give a colorless liquid: $^1$H NMR (500 MHz, $CDCl_3$) δ 2.9 (m, 2H), 4.3 (t, J=5.2, 2H), 5.6 (t, J=2.5, 1H), 6.2 (t, J=3.2, 1H); $^{13}$C NMR (125 MHz, $CDCl_3$) δ 171.49, 134.40, 122.98, 66.06, 28.16. $^1$H NMR spectra are reported in ppm downfield from tetramethylsilane; s=singlet, d=doublet, and br s=broad singlet.

Where indicated below, GC was used to determine % product relative to % starting material. With GC, response factors were assumed to be the same for both product and starting material. In addition to GC, NMR was also used to determine the relative percentages of product to starting material (data not shown).

The meaning of abbreviations is as follows: "μL" means microliter(s), "mL" means milliliter(s), "L" means liter(s), "mM" means millimolar, "M" means molar, "mmol" means millimole(s), "mol" means mole(s) and "min" means minute (s).

Example 1

Comparative Example

Use of α-Formyl Enolates for the Preparation of α-Methylene-γ-butyrolactone (3 Liter Scale)

A three-L, three-neck flask equipped with a mechanical stirrer and nitrogen inlet was charged with dry THF (1.0 L)

and sodium ethoxide (59 g, 0.87 mol) in 5 g portions. A thermometer and 250 mL addition funnel were attached. A solution of ethyl formate (64 g, 0.87 mol, 70 mL) and butyrolactone (75 g, 0.87 mol, 67 mL) were added at approximately 4 mL/min. After complete addition, the reaction was allowed to stir under nitrogen for one hour. The solid was filtered using a filter stick (C-frit), washed with THF (0.5 L), and filtered again to afford the sodium α-formyl-butyrolactone-enolate. The salt was suspended in THF (0.5 L) and paraformaldehyde (41 g, 1.7 mol) was added as a solid. A condenser was attached and the suspension heated at 65° C. for four hours. Please note: (i) a heating mantle was used and (ii) some paraformaldehyde may collect in the condenser. On cooling, the mixture filtered and filtrate concentrated in vacuo to afford crude α-methylene-γ-butyrolactone as an orange/brown liquid. Distillation at 0.5 torr/65° C. gave 37 g (43% yield) of pure material as a colorless liquid: $^1$H NMR (500 MHz, CDCl$_3$) δ 2.9 (m, 2H), 4.3 (t, J=5.2, 2H), 5.6 (t, J=2.5, 1H), 6.2 (t, J=3.2, 1H); δ $^{13}$C NMR (125 MHz, CDCl$_3$) δ 71.49, 134.40, 122.98, 66.06, 28.16; Analitically Calculated for C$_5$H$_6$O$_2$: C, 61.22; H 6.16. Found: C, 61.32, H, 6.33.

Example 2

Comparative Example

Use of α-Formyl Enolates for the Preparation of α-Methylene-γ-butyrolactone (20 Gallon Scale)

Like Example 1, but on a larger scale, to a twenty-gallon, glass-lined reactor equipped with a mechanical stirrer and nitrogen inlet was added THF (40 L) and sodium ethoxide (2.5 kg, 0.87 mol) in 100–150 g portions. A thermocouple, condenser, and three-L addition funnel were attached. A solution of ethyl formate (2731 g, 0.87 mol, 2978 mL) and butyrolactone (3175 g, 0.87 mol, 2834 mL) were added at approximately 40 mL/min. After complete addition, the reaction was allowed to stir overnight under a nitrogen blanket. The solid was filtered using a filter stick, washed with THF (10 L), and filtered again to afford the sodium α-formyl-butyrolactone-enolate salt. The salt was suspended in THF (20 L) and paraformaldehyde (1757 g, 1.7 mol) was added slowly as a solid in 50–100 g batches. After complete addition, the suspension was heated at 65° C. for four hours. On cooling, the mixture filtered and filtrate concentrated in vacuo to afford crude α-methylene-γ-butyrolactone as an orange/brown liquid. Distillation at 0.5 torr/65° C. gave 1.6 kg (44% yield) of α-methylene-γ-butyrolactone as a colorless liquid. α-Methylene-γ-butyrolactone prepared in this way contains up to 5% residual γ-butyrolactone by GC. In many cases the purity of α-methylene-γ-butyrolactone obtained after distillation was only 90% by GC and could not be increased by repeated distillations.

Example 3

Comparative Example

Use of α-Formyl Enolates for the Preparation of α-Methylene-γ-butyrolactone (150 Gallon Scale)

Like Example 1 and 2, but on a larger scale, to a 150-gallon, glass-lined reactor equipped with a mechanical stirrer and nitrogen inlet was added THF (318 L) and sodium ethoxide (25 kg, 368 mol) in 1 kg portions. A solution of ethyl formate (21.7 kg, 294 mol, 21.8 L) and butyrolactone (25.3 kg, 294 mol, 22.6 L) were added over three hours. After complete addition, the reaction was allowed to stir overnight under a nitrogen blanket. The liquid was filtered off using a filter stick, washed with THF (50 L), and filtered again to afford the sodium α-formyl-butyrolactone-enolate salt. The salt was suspended in THF (165 L) and paraformaldehyde (14.1 kg, 470 mol) was added over 1.5 hours. After complete addition, the suspension was heated at 65° C. for four hours. On cooling, the mixture filtered and filtrate concentrated in vacuo to afford crude α-methylene-γ-butyrolactone as an orange/brown liquid. Distillation at 0.5 torr/65° C. gave 9.2 kg (32% yield over two steps) of α-methylene-γ-butyrolactone as a colorless liquid. Please note that α-methylene-γ-butyrolactone prepared in this way contains up to 5% residual γ-butyrolactone by GC. Several other high boiling impurities are present at 1–2% levels. Residual dissolved formaldehyde caused clogging of the vacuum pump lines on distillation. This process was not reproducible.

Example 4

Comparative Example

Use of α-Oxalyl Enolates for the Preparation of α-Methylene-γ-butyrolactone (3 Liter Scale)

A three-L, three-neck flask equipped with a mechanical stirrer and nitrogen inlet was charged with dry THF (2.0 L) and sodium ethoxide (59 g, 0.87 mol) in 5 g portions. A thermometer and 250 mL addition funnel were attached. A solution of diethyl oxalate (127 g, 0.87 mol) and γ-butyrolactone (75 g, 0.87 mol) were added at approximately 3 mL/min. The oxalyl γ-butyrolactone sodium salt formed at ten minutes after the start of the addition. After complete addition, the reaction was allowed to stir under nitrogen for one hour and allowed to stand overnight at room temperature. The oxalyl γ-butyrolactone sodium salt formed as a solid white slurry in THF. This slurry could not be filtered to remove residual γ-butyrolactone and diethyl oxalate. On attempting to treat the crude slurry with formaldehyde, an intractable gel formed. The reaction mixture had to be discarded.

Example 5

Preparation of Ethyl Oxalyl γ-Butyrolactone Sodium Salt (150 Gallon Scale)

A 150-gallon, glass-lined reactor equipped with a mechanical stirrer and nitrogen inlet was charged with diethyl oxalate (32.7 kg, 224 mol), γ-butyrolactone (17.5 kg, 203 mol), and ethanol (160 L) and heated to 65° C. A 25 wt % solution of sodium methoxide in methanol (51.1 L) was added over three hours. After complete addition, the slurry was held at reflux for one hour. After cooling to 25° C., the slurry was filtered and the solid cake was washed with ethanol. The cake was dried overnight under a nitrogen stream at 40° C. to give 35 kg (82% yield) of the desired product as a white to pale yellow solid.

Example 6

Preparation of α-Methylene-γ-butyrolactone from Ethyl Oxalyl γ-Butyrolactone Sodium Salt (22 Liter Scale)

A 22-L, four-neck flask equipped with a mechanical stirrer and nitrogen inlet was charged with the oxalyl γ-butyrolactone sodium salt (3 kg, 14.4 mol) prepared in Example 5, potassium carbonate (750 g, 5.4 mol), water (4.0 L), methylene chloride (9.8 L), and cooled to 10° C. A 37 wt % of formaldehyde in water (1133 mL) was added over three hours. After complete addition, the slurry was held at 10° C. for 30 min. The slurry was filtered and the water layer (top) was separated from the filtrate. The methylene chloride layer (bottom) contained α-methylene-γ-butyrolactone in greater than 95% purity by GC. A polymerization inhibitor was added (typically 7 g Naugard® I-3 N,N'-bis(1,4-dimethylpentyl)-p-phenylenediamine, N-(1,4-dimethylpentyl)-N'-phenyl-p-phenylenediamine) from Uniroyal Co., Middlebury, Conn.) and the methylene chloride was removed in vacuo to give 1243 g (88%) of a dark liquid. Distillation at 0.5 torr/65° C. gave 1034 g (73% yield) of α-methylene-γ-butyrolactone as a colorless liquid with 99% purity by GC. There was less than 100 g of "distillation pot residue" in the three-L distillation flask.

Table 1 illustrates the reproducibility of the oxalate process for the preparation of α-methylene-γ-butyrolactone on a 22 L scale. All the reaction in Table 1 used the procedure described in Example 6.

TABLE 1

| Run | g MBL (crude) | final yield (%) after distillation |
|---|---|---|
| 1 | 1197 | 69 |
| 2 | 1194 | 72 |
| 3 | 1217 | 73 |
| 4 | 1173 | 73 |
| 5 | 1202 | 75 |
| 6 | 1243 | 73 |
| 7 | 1181 | 72 |
| 8 | 1138 | 65 |
| 9 | 1201 | 73 |
| 10 | 1202 | 74 |
| 11 | 1135 | 72 |
| 12 | 1178 | 74 |
| 13 | 1189 | 72 |
| 14 | 1141 | 71 |
| 15 | 1188 | 71 |
| 16 | 1154 | 68 |
| 17 | 1191 | 71 |
| 18 | 1129 | 70 |
| 19 | 1140 | 70 |
| 20 | 1185 | 72 |

Example 7

Preparation of Ethyl Oxalyl γ-Methyl-γ-butyrolactone Sodium Salt (22 Liter Scale)

A 22-L flask equipped with a mechanical stirrer and nitrogen inlet was charged with diethyl oxalate (1606 g, 11 mol), γ-methyl-γ-butyrolactone (1000 g, 10 mol) (Aldrich, St. Louis, Mo.), and ethanol (5.07 L) and heated to 65° C. A 25 wt % solution of sodium methoxide in methanol (2.5 L) was added over three hours. After complete addition, the slurry was held at reflux for one hour. After cooling to 25° C. and allowing to stand overnight, the slurry was filtered and the solid cake was washed with ethanol. The cake was dried overnight under a nitrogen stream at 40° C. to give 1920 g (86% yield) of the desired product as a white to pale yellow solid.

Example 8

Preparation of γ-Methyl-α-methylene-γ-butyrolactone From Ethyl Oxalyl γ-Methyl-γ-Butyrolactone Sodium Salt (5 Liter Scale)

A five-L, four-neck flask equipped with a mechanical stirrer and nitrogen inlet was charged with ethyl oxalyl γ-methyl-γ-butyrolactone sodium salt (750 g, 3.4 mol) from Example 7, potassium carbonate (116 g, 0.845 mol), water (942 mL), methylene chloride (2.3 L), and cooled to 10° C. A 37 wt % solution of formaldehyde in water (265 mL) was added over three hours. After complete addition, the slurry was held at 10° C. for 30 min. The slurry was filtered and the water layer (top) was separated from the filtrate. The methylene chloride layer (bottom) contained γ-methyl-α-methylene-γ-butyrolactone in greater than 95% purity by GC. A polymerization inhibitor was added (typically 1.9 g Naugard® I-3 from Uniroyal Co., Middlebury, Conn.) and the methylene chloride was removed in vacuo to give 316 g (84% yield) of a dark liquid. Distillation at 0.5 torr/65° C. gave 250 g (66% yield) of γ-methyl-α-methylene-γ-butyrolactone as a colorless liquid.

Example 9

Preparation of γ,γ-Dimethylbutyrolactone (For Example 10)

This procedure was adapted from: Cason, J., Adams, C., Bennett, L., Register, U. J. Am. Chem. Soc. 66:1764 (1944) and Arnold, R. Buckley, J. Richter, J. J. Am. Chem. Soc. 69:2322 (1947).

A jacketed one-liter reaction kettle equipped with a four blade 45 degree up flow mechanical stirrer, thermocouple, condenser and nitrogen inlet was charged with dry THF (250 mL) and ethyl levulinate (99% available Aldrich Chemical Company, Milwaukee, Wis.) (42 g, 0.288 mol). A 250 mL addition funnel was attached and the solution was cooled to 0° C. The addition funnel was charged via cannula with 250 mL of a 1.4 M solution of methyl magnesium bromide (0.35 mol, 1.2 eq) in 75/25 toluene/THF (v/v). The methylmagnesium bromide solution was added at 4 mL/min while maintaining reaction mass at −5 to 0° C. After stirring for two hours at 0° C., a solution of sulfuric acid (35 g, 0.35 mol, 1.2 eq) and 300 mL water was added at 7 mL/min while maintaining the reaction at >15° C. The solution was extracted with diethyl ether (2×150 mL) and the combined ether extracts washed with saturated NaCl solution (1×100 mL), dried over magnesium sulfate, and concentrated in vacuo to afford crude γ,γ-dimethylbutyrolactone as a dark orange oil. Distillation at 0.15 mm Hg/39° C. gave 22.3 g (67%) of pure material as a colorless liquid. $^1$H NMR (500 MHz, CDCl$_3$), 1.25 (s, 6H), 1.9 (t, 2H), 2.5 (t, 2H).

Example 10

Preparation of Ethyl Oxalyl γ,γ-Dimethyl-γ-butyrolactone Sodium Salt (5 Liter Scale)

A five-L flask equipped with a mechanical stirrer and nitrogen inlet was charged with diethyl oxalate (71.5 g, 0.49 mol), γ,γ-dimethyl-γ-butyrolactone (51 g, 0.43 mol) (prepared according to Example 9), and ethanol (312 mL) and heated to 65° C. A 25 wt % solution of sodium ethoxide in methanol (112 mL) was added over three hours. A portion of the distillate was removed via Dean Stark trap. A total of 246 mL of distillate was removed. After cooling to 25° C. and allowing to stand overnight, the slurry was filtered and the solid cake was washed with ethanol. The cake was dried overnight under a nitrogen stream at 40° C. to give 75.4 g (78% yield) of the desired product as a white to pale yellow solid.

Example 11

Preparation of γ,γ-Dimethyl-α-methylene-γ-butyrolactone from Ethyl Oxalyl γ,γ-Dimethyl, γ-Butyrolactone Sodium Salt (1 Liter Scale)

A one-L, four-neck flask equipped with a mechanical stirrer and nitrogen inlet was charged with ethyl oxalyl γ,γ-dimethyl-γ-butyrolactone sodium salt (100 g, 0.424 mol) from Example 9, potassium carbonate (14.6 g, 0.106 mol), water (118 mL), methylene chloride (288 mL), and cooled to 10° C. A 37 wt % solution of formaldehyde in water (33.3 mL) was added over 30 min. After complete addition, the slurry was held at 10° C. for 30 min. The slurry was filtered and the water layer (top) was separated from the filtrate. The methylene chloride layer (bottom) contained the γ,γ-dimethyl-α-methylene-γ-butyrolactone in greater than 95% purity by GC. A polymerization inhibitor was added (typically 1.9 g Naugard® I-3 from Uniroyal Co., Middlebury, Conn.) and the methylene chloride was removed in vacuo to give 51.7 g (97% yield) of a dark liquid. Distillation at 0.5 torr/65° C. gave 27 g (51% yield) of γ,γ-dimethyl-α-methylene-γ-butyrolactone as a colorless liquid.

Example 12

Preparation of α-Methylene-γ-butyrolactone (2 Liter Scale)

Reaction done in water and α-methylene-γ-butyrolactone was extracted in the workup:

A two-L, four-neck flask equipped with a mechanical stirrer and nitrogen inlet was charged with ethyl oxalyl γ-butyrolactone sodium salt (250 g, 1.2 mol), KHCO$_3$ (156 g, 1.56 mol), water (750 mL) and cooled to 10° C. A 37 wt % solution of formaldehyde in water (112 mL) was added over 30 min. After complete addition, the slurry was held at 10° C. for 30 min. The slurry was filtered and the filtrate was extracted with toluene (4×100 mL). The toluene extracts were combined and a polymerization inhibitor (0.1 g BHT) was added. After drying over magnesium sulfate, the solvent was removed in vacuo to afford 72 g (61% yield) α-methylene-γ-butyrolactone as a clear liquid (98 area % by GC). Distillation at 0.5 torr/65° C. gave 55 g (46% yield) of α-methylene-γ-butyrolactone as a colorless liquid (99 area % by GC).

Example 13

Preparation of α-Methylene-γ-butyrolactone (1 Liter Scale)

Reaction done in toluene with paraformaldehyde at reflux, no base was used:

A one-L, four-neck flask equipped with a mechanical stirrer and nitrogen inlet was charged with ethyl oxalyl γ-butyrolactone sodium salt (100 g, 0.51 mol), paraformaldehyde (23 g, 0.77 mol) and toluene (550 mL). The suspension was heated to reflux and held for one hour. The mixture was cooled to 50° C. and 200 mL water was added. The toluene layer was separated, dried over magnesium sulfate, and concentrated in vacuo to afford 39.4 g α-methylene-γ-butyrolactone (79% yield) as a pale yellow oil (89 area % by GC). The aqueous layer was extracted with toluene (2×100 mL), dried over magnesium sulfate, and concentrated in vacuo to afford an additional 10.7 g α-methylene-γ-butyrolactone as a pale yellow oil; The α-methylene-γ-butyrolactone fractions were combined and distilled at 0.5 torr/65° C. to afford 34 g (68%) α-methylene-γ-butyrolactone as a colorless liquid.

Example 14

Preparation of α-Methylene-γ-butyrolactone (1 Liter Scale)

Reaction done in acetonitrile with paraformaldehyde at reflux, no based used:

A 500-mL, four-neck flask equipped with a mechanical stirrer and nitrogen inlet was charged with ethyl oxalyl γ-butyrolactone sodium salt (50 g, 0.26 mol), paraformaldehyde (11.6 g, 0.39 mol) and acetonitrile (400 mL). The suspension was heated to reflux and held for one hour. The mixture was cooled to 50° C. and 100 mL water was added. The mixture was extracted with ethyl acetate, dried over magnesium sulfate, and concentrated in vacuo to afford 28 g crude α-methylene-γ-butyrolactone as a pale yellow oil (97 area % by GC). Distillation at 0.5 torr/65° C. gave 18.4 g (73%) α-methylene-γ-butyrolactone as a colorless liquid.

Example 15

Preparation of α-Methylene-γ-butyrolactone (1 Liter Scale)

Reaction done in ethanol with paraformaldehyde at reflux, no based used:

A one-L, four-neck flask equipped with a mechanical stirrer and nitrogen inlet was charged with ethyl oxalyl γ-butyrolactone sodium salt (50 g, 0.24 mol), paraformaldehyde (7.6 g, 0.25 mol) and ethanol (200 mL). The suspension was heated to reflux and held for one hour. The mixture was cooled and 100 mL saturated sodium hydrogencarbonate was added. The mixture was filtered through celite and filtrate extracted with toluene. The combined toluene extracts were dried over magnesium sulfate and concentrated in vacuo to afford 16.8 g (71% yield) α-methylene-γ-butyrolactone as a pale yellow liquid (97 area % by GC).

Example 16

Preparation of Ethyl Oxalyl γ-Butyrolactone Sodium Salt Using Sodium Ethoxide in Ethanol (1 Liter Scale)

(The oxalate methyl ester is not formed in this procedure because no methanol is used.)

A one-L, four-neck round bottom flask equipped with a mechanical stirrer and nitrogen inlet was charged with diethyl oxalate (46.7 g, 0.32 mol), γ-butyrolactone (25 g, 0.291 mol) and ethanol (250 mL) and heated to 82° C. A 21 wt % solution of sodium ethoxide in ethanol (130 mL) was added over one hour. After complete addition, the slurry was held at reflux for one hour. After cooling to 25° C., the slurry was filtered and the solid cake was washed with 100 mL ethanol. The cake was dried overnight under a nitrogen stream to afford 52 g (86%) of the desired product as a white solid.

Example 17

Preparation of Ethyl Oxalyl γ-Butyrolactone Sodium Salt Using Sodium Methoxide/Methanol in Ethyl Acetate (1 Liter Scale)

A one-liter, four-neck round bottom flask equipped with a mechanical stirrer and nitrogen inlet was charged with diethyl oxalate (85 g, 0.58 mol), γ-butyrolactone (50 g, 0.58 mol) and ethyl acetate (400 mL) and heated to 78° C. A 25 wt % solution of sodium methoxide in methanol (139 mL) was added over one hour. After complete addition, the slurry was held at reflux for one hour. After cooling to 25° C., the slurry was filtered and the solid cake dried overnight under a nitrogen stream to afford 83 g (68% yield) of the desired product as a white to pale yellow solid.

Example 18

Preparation of Ethyl Oxalyl γ-Butyrolactone Sodium Salt
No solvent, room temperature:

A one-liter, four-neck round bottom flask equipped with a mechanical stirrer and nitrogen inlet was charged with diethyl oxalate (178 g, 1.22 mol) and cooled to 0° C. A 25 wt % solution of sodium methoxide in methanol (279 mL) was added over ten min. To this was added γ-butyrolactone (100 g, 1.16 mol) over 10 min and the resulting solution was allowed to stand under nitrogen for eight hours. The solidified reaction mass was triturated with 2 L petroleum ether, filtered, and washed with 750 mL petroleum ether to afford 218 g (97% yield) of the desired product as a white solid.

Example 19

Preparation of α-Methylene-γ-butyrolactone in Ethyl Acetate in the Presence of Triethylamine Ethyl oxalyl γ-butyrolactone sodium salt (65 g, 0.313 mol) was suspended in 275 g of ethyl acetate and triethylamine (18.97 g, 0.188 mol, 0.6 eq) in a 500 mL round bottom flask equipped with a thermometer, mechancial stirrer, addition funnel and nitrogen purge system. Formalin (23.4 mL, 37 wt %, 0.313 mol), neutralized with potassium hydrogencarbonate and decanted) was added dropwise over eighteen min. After stirring for an additional hour, a coarse particle suspension formed. The solids were filtered over a Buchner funnel and before rotary evaporation of the solvent, 0.5 g of BHT polymerization inhibitor was added. The resulting thick oil after evaporation was vacuum distilled to collect 21.0 g of pure (98.3% by GC) α-methylene-γ-butyrolactone (69% yield).

Example 20

Effect of Triethylamine on Impurities in α-Methylene-γ-butyrolactone Synthesis in a Ethyl Acetate/Toluene Mixture Ethyl oxalyl γ-butyrolactone sodium salt (65 g, 0.313 mol) was suspended in 220 g of ethyl acetate, 68.5 g of toluene and triethylamine (see Table 2) in a 500 mL round bottom flask equipped with a thermometer, mechancial stirrer, addition funnel and nitrogen purge system. Formalin (23.4 mL, 37 wt %, 0.313 mol), neutralized with potassium hydrogencarbonate and decanted) was added dropwise over 15 min. After stirring for an additional hour, a coarse particle suspension formed. The solids were filtered over a Buchner funnel and before rotary evaporation of the solvent, 0.5 g of BHT polymerization inhibitor was added. The resulting thick oil after evaporation analyzed by GC for impurities which were identified by GC/MS.

TABLE 2

Effect of base on product ratios determined by GC

| Run | Triethylamine[1] | MBL[2] | Protonated salt[3] | Spiro compound[4] |
|---|---|---|---|---|
| 1 | 0.2 eq | 83 | 3 | 9 |
| 2 | 0.4 eq | 89 | 0 | 4 |
| 3 | 0.6 eq | 100 | 0 | 0 |

[1]Equivalents based on the starting oxalate salt
[2]Uncorrected for response
[3]α-ethyl oxalyl-γ-butyrolactone (Formula V)
[4]spiro compound (Formula VI)

Example 21

Synthesis of Sodium; Methoxycarbonyl-(5-pentyl-2-oxo-dihydro-furan-3-ylidene)-methanolate (Pentyl-GBL-oxalate Salt)

A 2 L flask with a thermometer, mechanical stirrer, addition funnel and nitrogen purge system was charged with diethyl oxalate (93.6 g, 0.641 mole), ethanol (464 g) and γ-nonanoic lactone (pentyl GBL, 100 g, 0.641 mole). The flask was heated to 80° C. and sodium methoxide in methanol (25 wt %, 145.4 g, 0.673 mole) was added dropwise over two hours via the addition funnel. After 75 min, the reaction mass became a thick slurry at which point 500 mL of ethanol was added. The resulting suspension was filtered over glass fritted funnels and dried under a nitrogen stream to afford 158.6 g (94% yield) of a mixture of ethyl and methyl oxalate salt in 1:1 ratio, each with 3.3:1 Z/E ratio. $^1$H-NMR (DMSO) δ (ppm): 0.88 (t, 3H, J=7.7 Hz, CH$_3$), 1.1 ppm (t, 3H, J=7 Hz, CH$_3$, ethyl ester, E isomer), 1.2 (t, 3H, J=7 Hz, CH$_3$, ethyl ester, Z isomer), 1.25–1.6 (m, 8H, CH$_2$), 2.2 (m, 1H, OCH$_2$), 2.66 (m, 1H, OCH$_2$), 3.53 (s, 3H, OCH$_3$, E isomer), 3.64 (s, 3H, OCH$_3$, Z isomer), 4.0 (q, 3H, J=7 Hz, OCH$_2$, ethyl ester, Z isomer), 4.11 (m, 1H, CH and 2H, OCH$_2$, ethyl ester, E isomer).

Example 22

Synthesis of 3-Methylene-5-pentyl-dihydro-furan-2-one (Pentyl-MBL)

The pentyl-GBL salt (160 g, 0.575 mol) from Example 21 was suspended in 1,850 g of toluene and 34.9 g of triethylamine (0.345 mole) in a 2-L round bottom flask equipped with a thermometer, mechanical stirrer, addition funnel and nitrogen purge system. To this was added 46.6 g of formalin (37 wt %, 0.575 mole, neutralized with potassium hydrogencarbonate) dropwise over 30 minutes. After stirring for an additional hour, the reaction mass was filtered over a bed of Celite® filtering product (of World Minerals Co., Lompoc, Calif.). Before rotary evaporation of the solvent, 0.5 g of Naugard® I-3 (of Uniroyal Co., Middlebury, Conn.) polymerization inhibitor was added. The resulting thick oil (containing 92% product by GC) was vacuum distilled to collect 35 g of pure (97.5% by GC) pentyl-MBL (bp 69° C. at 190 millitorr). $^1$H-NMR (DMSO) δ (ppm): 0.88 (t, 3H, J=7.7 Hz, CH$_3$), 1.29 (m, 6H, CH$_2$), 1.6 (m, 2H, CH$_2$), 2.6 (m, 1H, OCH$_2$), 3.1 (m, 1H, OCH$_2$), 4.54 (p, 1H, J=7.3 Hz, CH), 5.70 (s, 1H,=CH$_2$), 6.00 (s, 1H,=CH$_2$). $^{13}$C-NMR (DMSO) δ (ppm): 12.45 (—CH$_3$), 20.63 (—CH$_2$—), 23.12 (—CH$_2$), 29.67 (—CH$_2$—), 34.11 (—CH$_2$—), 75.92 (CH$_2$—O—), 119.81 (H$_2$C=), 134.08 (—C=CH$_2$), 168.39 (C=O).

What is claimed is:

1. A process for preparing α-metlhylenelactoncs of Formula III comprising the steps:

(a) contacting lactones of Formula I with an oxalate in the presence of a base and a solvent to form an intermediate mixture comprising the compound of Formula II and isolating the compound of Formula II from the intermediate mixture;

(b) treating the isolated compound of Formula II with formaldehyde to form a product mixture; and (c) optionally isolating the α-methylenelactones of Formula III from the product mixture,

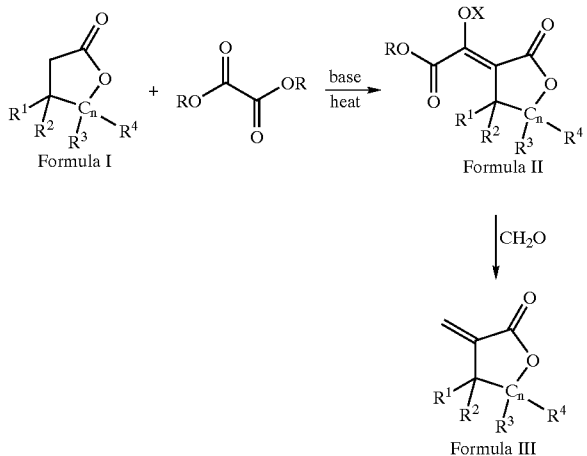

Formula I + Formula II

↓ CH₂O

Formula III wherein,
n=1–11;
X is a cation;
R is hydrocarbyl or substituted hydrocarbyl;
$R^1$, $R^2$, $R^3$ and $R^4$ independently are hydrogen, hydrocarbyl or substituted hydrocarbyl.

2. A process according to claim 1 wherein any two of $R_1$, $R^2$, $R^3$ and $R^4$ are joined to form a ring structure selected from the group consisting of, hydrocarbyl or substituted hydrocarbyl.

3. A process according to claim 1 wherein the lactone of Formula I is γ-butyrolactone and the α-methylenelactone of Formula III is α-methylene-γ-butyrolactone.

4. A process according to claim 1 wherein $R^3$ is $CH_3$.

5. A process according to claim 1 wherein both $R^3$ and $R^4$ are $CH_3$.

6. A process according to claim 1 wherein $R^3$ is $CH_2CH_2CH_2CH_2CH_3$.

7. A process according to claim 1 wherein the base is selected from the group consisting of metal alkoxides, metal oxides, hydroxides, carbonates, phosphates and mixtures thereof.

8. A process according to claim 1 wherein the base is selected from the group consisting of sodium methoxide, sodium ethoxide, sodium isopropoxide, sodium n-butoxide, potassium carbonate, cesium carbonate, sodium carbonate, barium carbonate, sodium hydrogen carbonate, magnesium oxide, barium oxide, barium hydroxide, lanthanum oxide, potassium hydroxide, cadmium oxide, rubidium oxide, lithium hydroxide, strontium hydroxide, sodium hydroxide, calcium hydroxide, potassium hydroxide, potassium phosphate and mixtures thereof.

9. A process according to claim 1 wherein the base is selected from the group consisting of sodium methoxide, sodium ethoxide, sodium isopropoxide and sodium hydroxide.

10. A process according to claim 1 wherein the base is supported on a suitable support.

11. A process according to claim 10 wherein the suitable support is selected from the group consisting of silica, titania, zirconia, alumina, carbon, zeolites and mixtures thereof.

12. A process according to claim 1 wherein the formaldehyde is elected from the group consisting of formalin, 2-ethylhexylhemiformal, araformaldehyde, trioxane, acetals and polyacetals.

13. A process according to claim 1 wherein the lactone and the oxalate are heated at a temperature greater than about 25° C. and pressure of 2000 psi or lower.

14. A process according to claim 1 wherein the base is homogeneous.

15. A process according to claim 1 wherein the base is heterogeneous.

16. A process according to claim 1 wherein the solvent is selected from the group consisting of toluene, methylene chloride, acetone, acetonitrile, ethyl acetate, ethanol, isopropanol, methanol, 2,2-diethoxypropane, n-butanol, polyethylene glycols, and mixtures thereof.

17. A process according to claim 1 wherein the solvent is selected from the group consisting of toluene, methylene chloride, acetone, acetonitrile, ethyl acetate, ethanol, isopropanol, methanol, 2,2-diethoxypropane, n-butanol, polyethylene glycols, water, and mixtures thereof.

18. A process according to claim 1 wherein the intermediate mixture is optionally heated.

19. A process according to claim 1 further comprising contacting a phase transfer catalyst with the lactones of Formula I and the oxalate in the presence of a base and a solvent to form the intermediate mixture comprising the compound of Formula II.

20. A process according to claim 19 wherein the phase transfer catalyst is selected from the group consisting of quaternary ammonium salts, quaternary phosphonium salts, crown ethers, and polyethers.

21. A process according to claim 1 further comprising contacting the isolated compound of Formula II with a phase transfer catalyst before treating the isolated compound of Formula II with the formaldehyde to form a product mixture.

22. A process according to claim 1 wherein a base is further added to the compound of Formula II and the formaldehyde to form the product mixture.

23. A process according to claim 22 wherein the base is selected from the group consisting of potassium hydrogencarbonate and triethylamine.

24. A process for preparing α-substituted hydrocarbylidene lactones of Formula IV comprising the steps:

(a) contacting lactones of Formula I with an oxalate in the presence of a base and a solvent to form an intermediate mixture comprising the compound of Formula II and isolating the compound of Formula II from the intermediate mixture;

(b) treating the isolated compound of Formula II with a formaldehyde derivative to form a product mixture; and (c) optionally isolating the α-substituted hydrocarbylidene lactones of Formula IV from the product mixture.

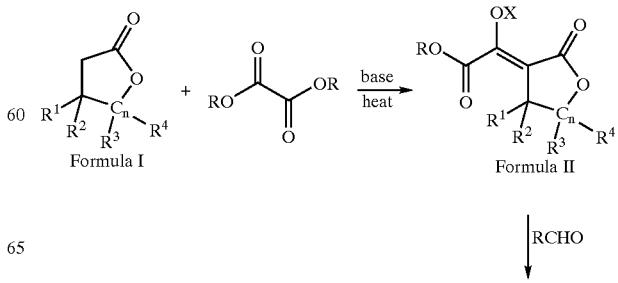

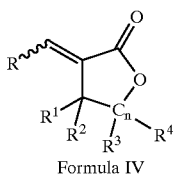

Formula IV wherein,
n=1–11;
R is hydrocarbyl or substituted hydrocarbyl;
X is a cation; and
$R_1$, $R^2$, $R^3$ and $R^4$ taken independently are hydrogen, hydrocarbyl or substituted hydrocarbyl.

25. A process according to claim 24 wherein any two of $R^1$, $R^2$, $R^3$ and $R^4$ form a ring structure selected from the group consisting of, unsubstituted or substituted cycloalkyl, unsubstituted or substituted cycloalkyl containing at least one heteroatom in the ring, unsubstituted or substituted aromatic ring, and unsubstituted or substituted aromatic ring containing at least one heteroatom in the ring.

26. A process according to claim 24 wherein the formaldehyde derivative is a substituted aldehyde.

27. A process according to claim 26 wherein the substituted aldehyde is selected from the group consisting of acetaldehyde, propionaldehyde, butyraldehyde, isobutyraldehyde, n-pentanal, 2-methylbutanal, 3-methylbutanal, n-hexanal, 2-methylpentanal, 3,3-dimethylbutanal, 2-ethylhexanal, 2-methyldecanal, glyoxal, methylglyoxal, malonic dialdehyde, succinic dialdehyde and glutaric dialdehyde, 3-hydroxy-2,2-dimethylpropanol, methoxypivalaldehyde, butoxypivalaldehyde, 4-acetoxybutyaldehyde and 5-formylvaleraldehyde.

28. A process according to claim 24 wherein the base is selected from the group consisting of metal alkoxides, metal oxides, hydroxides, carbonates, phosphates, and mixtures thereof.

29. A process according to claim 24 wherein the base is selected from the group consisting of sodium methoxide, sodium ethoxide, sodium isopropoxide, sodium n-butoxide, potassium carbonate, cesium carbonate, sodium carbonate, barium carbonate, sodium hydrogen carbonate, magnesium oxide, barium oxide, barium hydroxide, lanthanum oxide, potassium hydroxide, cadmium oxide, rubidium oxide, lithium hydroxide, strontium hydroxide, sodium hydroxide, calcium hydroxide, potassium hydroxide, potassium phosphate, and mixtures thereof.

30. A process according to claim 24 wherein the base is supported on a suitable support.

31. A process according to claim 30 wherein the base comprises a catalyst promoter.

32. A process according to claim 30 wherein the suitable support is selected from the group consisting of silica, titania, zirconia, alumina, carbon, zeolites and mixtures thereof.

33. A process according to claim 24 wherein the lactone and the oxalate are heated at a temperature greater than about 25° C. and a pressure of less than or equal to 2000 psi.

34. A process according to claim 24 wherein the base is homogeneous.

35. A process according to claim 24 wherein the base is heterogeneous.

36. A process according to claim 24 further comprising contacting a phase transfer catalyst with the lactones of Formula I and the oxalate in the presence of a base and a solvent to form an intermediate mixture comprising the compound of Formula II.

37. A process according to claim 24 wherein the intermediate mixture is optionally heated.

38. A process according to claim 24 further comprising contacting the isolated compound of Formula II with a phase transfer catalyst before treating the isolated compound of Formula II with the formaldehyde to form a product mixture.

39. A process according to claim 1 or 24 wherein the α-methylene-lactones or α-substituted hydrocarbylidene lactones are isolated from the product mixture by a depolymerization process comprising the steps of:
(a) adding a free radical initiator to the product mixture at a temperature sufficient to form a polymer mixture comprising α-methylenelactone or α-substituted hydrocarbylidene lactone homopolymers;
(b) isolating the α-methylenelactones or α-substituted hydrocarbylidene lactone homopolymers from the polymer mixture; and
(c) heating the isolated α-methylenelactone or α-substituted hydrocarbylidene lactone polymers to at least 200° C. to ok the α-methylenelactone or α-substituted hydrocarbylidene lactone monomers.

40. A process according to claim 1 or 24 wherein the α-methylene-lactones or α-substituted hydrocarbylidene lactones are isolated by a steam distillation process comprising the steps of:
(a) contacting the product mixture containing the α-methylene-lactones or α-substituted hydrocarbylidene lactones with steam wherein the steam and α-methylenelactones or α-substituted hydrocarbylidene lactones form a steam mixture;
(b) distilling the steam mixture to form a distillate;
(c) contacting the distillate with a solvent to extract the α-methylenelactones or α-substituted hydrocarbylidene lactones from the distillate; and
(d) optionally repeating step (c).

41. A process according to claim 1 or 24 wherein the α-methylene-lactones or α-substituted hydrocarbylidene lactones are isolated by a melt crystallization process comprising the steps of:
(a) cooling the product mixture below the melting point of the α-methylenelactones or α-substituted hydrocarbylidene lactones to form a mixture comprising α-methylenelactones or α-substituted hydrocarbylidene lactones in a solid state and residual lactones in a solution state;
(b) washing away the residual lactones from the solid α-methylenelactones or α-substituted hydrocarbylidene lactones; and
(c) heating the solid α-methylenelactones or α-substituted hydrocarbylidene lactones of step (b) to recover the α-methylenelactones of Formula III or α-substituted hydrocarbylidene lactones of Formula IV in a liquid state.

42. The process of claim 1 wherein $R_1$, $R^2$, $R^3$ and $R^4$ are independently selected from $C_1$–$C_{18}$ unsubstituted or substituted alkyl, unsubstituted or substituted alkenyl, unsubstitlited or substituted cycloalkyl, unsubstituted or substituted cycloalkyl containing at least one heteroatom, unsubstituted or substituted aromatic ring, and unsubstituted or substituted aromatic ring containing at least one heteroatom.

43. The process of claim 1 wherein any two of $R_1$, $R^2$, $R^3$ and $R^4$ are joined to form a ring stricture selected from the group consisting of unsubstituted or substituted cycloalkyl, unsubstituted or substituted cycloalkyl containing at least one heteroatom in the ring, unsubstituited or substituted aromatic ring, and unsubstituted or substituted aromatic ring containing at least one heteroatom in the ring.

44. The process of claim 24 wherein $R^1$, $R^2$, $R^3$ and $R^4$ are independently selected from $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aromatic ring, and unsubstituted or substituted aromatic ring containing at least one heteroatom.

* * * * *